(12) United States Patent
Tobita

(10) Patent No.: US 8,303,968 B2
(45) Date of Patent: Nov. 6, 2012

(54) WATER-IN-OIL TYPE EMULSIFIED COMPOSITION

(75) Inventor: Kazuhiko Tobita, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 315 days.

(21) Appl. No.: 12/101,234

(22) Filed: Apr. 11, 2008

(65) Prior Publication Data

US 2008/0280865 A1 Nov. 13, 2008

(30) Foreign Application Priority Data

Apr. 11, 2007 (JP) ................................. 2007-103686

(51) Int. Cl.
*A61Q 17/04* (2006.01)
(52) U.S. Cl. .......................................... 424/401; 424/59
(58) Field of Classification Search .................... None
See application file for complete search history.

(56) References Cited

U.S. PATENT DOCUMENTS

2007/0037728 A1   2/2007   Kunieda et al.

FOREIGN PATENT DOCUMENTS

| EP | 1044676 | * 10/2000 |
|---|---|---|
| JP | 61-129033 | 6/1986 |
| JP | A 03-95107 | 4/1991 |
| JP | 8-20529 | 1/1996 |
| JP | 11-240828 | 9/1999 |
| JP | 2000-355531 | 12/2000 |
| JP | 2002-121105 | 4/2002 |
| JP | 2004-026748 | 1/2004 |
| JP | 3802288 | 5/2006 |
| JP | 2006-169130 | * 6/2006 |
| JP | 2006-306868 | 11/2006 |

OTHER PUBLICATIONS

Japanese Office Action dispatched Jan. 4, 2012 in corresponding Japanese Patent Application No. 2007-103686 with English Translation, (8 pp.).
Japanese Office Action dispatched Jul. 3, 2012 in corresponding Japanese Patent Application No. 2007-103686. English Translation Only, (3 pp.).

* cited by examiner

*Primary Examiner* — Jyothsna Venkat
(74) *Attorney, Agent, or Firm* — Oblon, Spivak, McClelland, Maier & Neustadt, L.L.P.

(57) ABSTRACT

Water-in-oil type emulsified compositions with a high silicone oil content which are excellent in emulsification stability and whose sticky feeling has been improved may be obtained by incorporating a specific (A) N-long chain acyl neutral amino acid ester, (B) a silicone oil, and (C) water therein.

12 Claims, No Drawings

WATER-IN-OIL TYPE EMULSIFIED COMPOSITION

CROSS REFERENCES TO RELATED APPLICATIONS

This application claims priority to Japanese Patent Application No. 103686/2007, filed on Apr. 11, 2007, which is incorporated herein by reference in its entirety.

BACKGROUND OF THE INVENTION

1. Field of the Invention

The present invention relates to water-in-oil type emulsified compositions, and further to cosmetics which contain such a water-in-oil type emulsified composition.

2. Discussion of the Background

A water-in-oil type emulsified cosmetic has an outer layer composed of an oil component. Therefore, while it has advantages that it protects the skin, imparts flexibility and the like, it has had problems that when it is stored at a high temperature, the system is destabilized to cause water droplet coalescence or phase separation, and when it is applied to the skin, a sticky feeling may be provided because the outer phase is an oil. It has been a matter of common knowledge that by incorporating a silicone oil at a high content, such a sticky feeling can be eliminated. However, emulsification of a silicone oil per se is extremely difficult, and various attempts to stabilize emulsification have been carried out in the past.

JP-A-2006-169130 and JP-A-2006-306868 disclose a water-in-oil type emulsified composition with a high silicone oil content containing a specific emulsifying agent in order to obtain a water-in-oil type emulsified composition which is excellent in a feeling of use. However, the emulsifying agent that can be used for preparing such a water-in-oil type emulsified composition is extremely limited, and it is necessary to incorporate also a surfactant therein at a high content, etc. Therefore, it could not necessarily be declared that this technique is a general-purpose technique.

Further, JP-A-61-129033 discloses a technique for stabilizing a water-in-oil type emulsified composition using a clay mineral obtained by a treatment with a quaternary ammonium salt. Further, JP-A-8-20529 discloses that an extremely stable water-in-oil type emulsified composition can be obtained when an N-long chain acyl acidic amino acid ester and an organic modified clay mineral obtained by a treatment with a quaternary ammonium salt are incorporated therein. However, there is no examples in which a silicone oil has been incorporated at a high content as an oil phase, and in the case where a silicone oil is incorporated at a high content, an emulsified composition cannot be obtained, etc. Therefore, it could not be declared that this technique is a technique that can be applied to a silicone oil.

On the other hand, Japanese Patent No. 3802288 discloses an N-long chain acyl neutral amino acid ester. However, although such an N-long chain acyl neutral amino acid ester is known as an oily material with a high safety, it has not been known at all in the past that the N-long chain acyl neutral amino acid ester has an emulsifying ability.

Thus, a water-in-oil type emulsified composition with a high silicone oil content which is excellent in emulsification stability and whose sticky feeling has been improved remains eagerly awaited.

SUMMARY OF THE INVENTION

Accordingly, it is one object of the present invention to provide novel water-in-oil type emulsified compositions.

It is another object of the present invention to provide novel water-in-oil type emulsified compositions with a high silicone oil content.

It is another object of the present invention to provide novel water-in-oil type emulsified compositions with a high silicone oil content, which exhibit excellent emulsification stability.

It is another object of the present invention to provide novel water-in-oil type emulsified compositions with a high silicone oil content, which exhibit an improvement in regard to sticky feeling.

It is another object of the present invention to provide novel water-in-oil type emulsified compositions with a high silicone oil content, which exhibit excellent emulsification stability and an improvement in regard to sticky feeling.

It is another object of the present invention to provide novel cosmetics which contain such a water-in-oil emulsified composition.

These and other objects, which will become apparent during the following detailed description, have been achieved by the inventor's discovery that compositions which comprise (A) at least one N-long chain acyl neutral amino acid ester, (B) at least one silicone oil, and (C) water, exhibit excellent emulsification stability and an improvement in regard to sticky feeling.

Thus, the present invention provides following embodiments:

(1) A water-in-oil type emulsified composition, which comprises:

(A) at least one N-long chain acyl neutral amino acid ester represented by the following general formula (I):

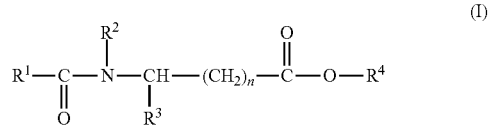

wherein $R^1$ represents a branched-chain or straight-chain alkyl group or alkenyl group having 5 to 21 carbon atoms, $R^2$ represents a hydrogen atom or an alkyl group having 1 to 3 carbon atoms, $R^3$ represents a hydrogen atom, a methyl group, an ethyl group, a branched-chain or straight-chain alkyl group having 3 to 4 carbon atoms, or a hydroxymethyl or hydroxyethyl group, $R^4$ represents a branched-chain or straight-chain alkyl group or alkenyl group having 1 to 34 carbon atoms or an alcohol residue of a sterol, and n represents an integer of 0 to 2;

(B) at least one silicone oil; and (C) water, wherein an outer phase comprises said (B) at least one silicone oil.

(2) A water-in-oil type emulsified composition according to (1), wherein the weight ratio of component (A) to component (B) is from 4:96 to 90:10, and component (C) is present in an amount of from 0.1 to 94.6 wt. % based on the total weight of component (A), component (B), and component (C).

(3) The water-in-oil type emulsified composition according to (1) or (2), wherein said component (A) is one or more N-long chain acyl esters of a neutral amino acid selected from the group consisting of glycine, alanine, N-methyl-β-alanine, threonine, and sarcosine.

(4) The water-in-oil type emulsified composition according to (1) or (3), wherein said component (A) is one or more members selected from the group consisting of N-myristoyl-N-methyl-β-alanine phytosteryl and N-myristoyl-N-methyl-β-alanine decyltetradecyl.

(5) The water-in-oil type emulsified composition according to any one of (1) to (4), wherein said component (B) is a cyclic silicone oil.

(6) A cosmetic comprising the water-in-oil type emulsified composition according to any one of (1) to (5).

By incorporating a specific N-long chain acyl neutral amino acid ester, a silicone oil, and water, it became possible to provide a water-in-oil type emulsified composition which is excellent in emulsification stability and whose sticky feeling has been improved.

DETAILED DESCRIPTION OF THE PREFERRED EMBODIMENTS

The component (A) to be used in the present invention is at least one N-long chain acyl neutral amino acid ester represented by the following general formula (I):

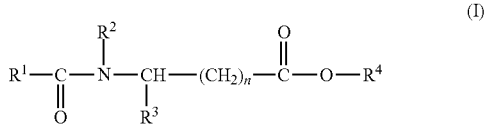

wherein $R^1$ represents a branched-chain or straight-chain alkyl group or alkenyl group having 5 to 21 carbon atoms, $R^2$ represents a hydrogen atom or an alkyl group having 1 to 3 carbon atoms, $R^3$ represents a hydrogen atom, a methyl group, an ethyl group, a branched-chain or straight-chain alkyl group having 3 to 4 carbon atoms, or a hydroxymethyl or hydroxyethyl group, $R^4$ represents a branched-chain or straight-chain alkyl group or alkenyl group having 1 to 34 carbon atoms or an alcohol residue of a sterol, and n represents an integer of 0 to 2.

The N-long chain acyl neutral amino acid ester which is component (A) to be used in the invention can be easily obtained by a known method described in, for example, Japanese Patent No. 2990624, Japanese Patent No. 3802288, or the like. To be more specific, a method in which a neutral amino acid and a fatty acid halide are reacted with each other through the Schotten-Baumann reaction, and then an alcohol or a sterol is esterified is widely known.

As the neutral amino acid of component (A), glycine, alanine, N-methyl-β-alanine, threonine, sarcosine, β-alanine, phenylalanine, proline, valine, leucine, isoleucine, serine, hydroxyproline, aminobutyric acid, aminocaproic acid, or the like can be used. These amino acids may be in the L-form, D-form, or DL-form. Among these, one kind may be used, or two or more kinds selected from the above-mentioned group may be used as a mixture. From the viewpoint that the stability and the feeling of use of the material after esterification are favorable, N-methyl-β-alanine is preferred.

As the acyl group of component (A), a straight-chain or branched-chain group derived from a saturated or unsaturated fatty acid having 8 to 22 carbon atoms can be used. For example, as the fatty acid, caprylic acid, capric acid, lauric acid, myristic acid, stearic acid, isostearic acid, palmitic acid, oleic acid, linoleic acid, behenic acid, coconut oil fatty acid, palm fatty acid, hydrogenated beef tallow fatty acid, and the like can be exemplified. Among these, one kind may be used, or two or more kinds selected from the above-mentioned group may be used as a mixture. In particular, from the viewpoint that a water-in-oil type emulsified composition having a good stability is obtained, lauric acid, myristic acid, and palm fatty acid are preferred, and particularly myristic acid is preferred.

As the hydrocarbon group ($R^4$) constituting an alcohol moiety of the N-long chain acyl neutral amino acid ester as component (A), a branched-chain or straight-chain alkyl group or alkenyl group having 1 to 34 carbon atoms or a sterol can be used. Examples thereof include groups derived from methanol, ethanol, propanol, isopropanol, butanol, t-butanol, isobutanol, 3-methyl-1-butanol, 2-methyl-1-butanol, fusel oil, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, arachyl alcohol, behenyl alcohol, jojoba alcohol, 2-hexadecyl alcohol, 2-octyldodecanol, isostearyl alcohol, decyltetradecanol, tetradecyloctadecanol, cholesterol, dihydrocholesterol, sitosterol, campesterol, stigmasterol, phytosterol, and lanosterol. Among these, preferred are isostearyl alcohol, decyltetradecanol, tetradecyloctadecanol, behenyl alcohol, phytosterol, cholesterol, and sitosterol, and particularly preferred are decyltetradecanol and phytosterol. Among these, one kind may be used, or two or more kinds selected from the above-mentioned group may be used as a mixture. These may be any of animal-derived substances, plant-derived substances, and synthetic substances.

The silicone oil as component (B) is not particularly limited, however, a solid or liquid silicone oil which is used in common cosmetics can be used. Specific examples thereof include polysiloxanes such as methylpolysiloxane, highly polymerized methylpolysiloxane, dimethylpolysiloxane, methylphenylpolysiloxane, methylhydrogenpolysiloxane, methylcyclopolysiloxane, polyoxyethylene/methylpolysiloxane copolymers, crosslinked methylpolysiloxane, and crosslinked methylphenylpolysiloxane; modified silicones such as polyether-modified silicones, fatty acid-modified silicones, acrylic-modified silicones, fluorine-modified silicones, amino-modified silicones, and alkyl-modified silicones; cyclic silicones such as decamethyltetrasiloxane, octamethylcyclotetrasiloxane, octamethylcyclopentasiloxane, decamethylcyclopentasiloxane, dodecamethylcyclohexasiloxane, and methylcyclopolysiloxane; and the like. Among these, one kind may be used, or two or more kinds selected from the above-mentioned group may be used as a mixture. From the viewpoint that a water-in-oil type emulsified composition which is stable regardless of other conditions is easily obtained, preferred are liquid silicones, more preferred are cyclic silicones, further more preferred are decamethyltetrasiloxane, octamethylcyclotetrasiloxane, octamethylcyclopentasiloxane, decamethylcyclopentasiloxane, dodecamethylcyclohexasiloxane, and methylcyclopolysiloxane, still further more preferred are decamethylcyclopentasiloxane and dodecamethylcyclohexasiloxane, and particularly preferred is decamethylcyclopentasiloxane.

The water as component (C) to be used in the invention is not particularly limited as long as it has a purity to such an extent that it can be commonly used in a washing agent or a cosmetic. Specifically, ion exchanged water, well water, natural water, groundwater, tap water, hard water, soft water, or the like can be used. Among these, one kind may be used, or two or more kinds selected from the above group may be used as a mixture. From the viewpoint of the storage stability of the present inventive product or an aspect of hygiene, ion exchanged water is preferred.

The weight ratio of component (A) to component (B) to be used in the invention is not particularly limited as long as a water-in-oil type emulsified composition is formed, however, it is preferably from 4:96 to 90:10. When the weight ratio of component (A) is less than 4, a sufficient emulsified state cannot be obtained to cause phase separation in some cases, and when the weight ratio of component (A) is more than 90, a decrease in the fluidity is caused in some cases. From the viewpoint that a stable water-in-oil type emulsified composition is obtained, the weight ratio of component (A) to component (B) is more preferably from 5:95 to 80:20, further more preferably from 6:94 to 75:25.

The weight of component (C) to be used in the invention is not particularly limited as long as a water-in-oil type emulsified composition is formed, however, it is preferably from 0.1 to 94.6% by weight based on the total weight of components (A), (B), and (C). When the weight of component (C) is less than 0.1% by weight, it is difficult to practically form an emulsified composition in some cases, and when it is more than 94.6% by weight, water release may be caused in some cases. From the viewpoint that a stable water-in-oil type emulsified composition is obtained, the weight of component (C) is more preferably from 0.5 to 90 wt. %, and particularly preferably from 1.0 to 80 wt. %, based on the total weight of components (A), (B), and (C).

The water-in-oil type emulsified composition of the invention can be used as a cosmetic such as a sunscreen cream, a moisturizing cream, a makeup remover, a liquid foundation or a foundation cream.

In the water-in-oil type emulsified composition of the invention, other than the above-mentioned essential components, a variety of optional components which are used in a common cosmetic, quasi drug or the like, for example, oily components such as hydrocarbons, higher fatty acid esters, animal and vegetable oils and fats, and fluorinated oils, powders such as organic pigments and inorganic pigments, aqueous components such as water-soluble polymers and alcohols, surfactants, ultraviolet light absorbers, moisturizing agents, antioxidants, beautifying components, preservatives, perfumes and the like can be appropriately incorporated to such an extent that the effect of the invention is not impaired.

As the oily component, other than a silicone oil which is an essential component, a solid oil, a semi-solid oil, a liquid oil, a volatile oil or the like which is commonly used in a cosmetic can be used. Examples thereof include hydrocarbons, oils and fats, waxes, hydrogenated oils, esters, fatty acids, higher alcohols, fluorinated oils, lipophilic surfactants and the like. It does not matter whether these are animal oils, vegetable oils, minerals oils or synthetic oils. Specific examples thereof include solid paraffin wax, microcrystalline wax, carnauba wax, ceresin wax, beeswax, Japan tallow, whale tallow, polyethylene wax, liquid paraffin, squalane, polybutene, polyisobutene, petrolatum, olive oil, castor oil, jojoba oil, macadamia nut oil, pentaerythritol rosinate ester, dipentaerythritol fatty acid esters, cholesterol fatty acid esters, phytosterol fatty acid esters, lanolin, isopropyl myristate, isopropyl palmitate, cetyl 2-ethylhexanoate, octyldodecyl myristate, glyceryl trioctanoate, diglyceryl polyisostearate, stearic acid, lauric acid, myristic acid, behenic acid, isostearic acid, oleic acid, cetyl alcohol, stearyl alcohol, lauryl alcohol, isostearyl alcohol, oleyl alcohol, perfluorooctane, perfluorodecane, perfluoropolyether, glyceryl monostearate, sorbitan tristearate, and the like.

The powder is not particularly limited in terms of its form as long as it is a powder which is commonly used in a cosmetic, and any powder in the form of a sphere, a plate, a needle or the like can be used. Examples thereof include inorganic powders such as talc, kaolin, mica, synthetic mica, sericite, magnesium carbonate, calcium carbonate, aluminum silicate, magnesium silicate, aluminum magnesium silicate, anhydrous silicic acid, silicon carbide, barium sulfate, bentonite, smectite, titanium oxide, zinc oxide, magnesium oxide, aluminum oxide, red iron oxide, yellow iron oxide, black iron oxide, titanium oxide, chromium oxide, iron blue pigment, ultramarine blue pigment, mica iron oxide, titanium mica iron oxide, titanium mica, and bismuth oxychloride; organic powders such as nylon powders, polyethylene powders, polystyrene powders, methylmethacrylate powders, polytetrafluoroethylene powders, wool powders, silk powders, crystalline cellulose, tar pigments, and lake pigments thereof; and powders obtained by forming a composite of one kind or two or more kinds of these powders. Further, a powder subjected to a surface treatment using one kind or two or more kinds of fluorine compounds, silicone oil agents, metal soaps, waxes, oils and fats, hydrocarbons and the like can also be used.

The aqueous component is not particularly limited and any can be used as long as it is a water-soluble component which is commonly used in a cosmetic. Examples thereof include glycerols such as glycerin, diglycerin and polyglycerin; glycols such as propylene glycol, dipropylene glycol, butylene glycol, and polyethylene glycol; saccharides such as sorbitol, sucrose, and maltitol; water-soluble polymers such as guar gum, gum arabic, carrageenan, sodium alginate, sodium chondroitin sulfate, methyl cellulose, hydroxyethyl cellulose, carboxymethyl cellulose, carboxyvinyl polymers, polyvinyl alcohols, polyvinylpyrrolidone, alkylated carboxyvinyl polymers, and sodium polyacrylate; salts such as sodium chloride, magnesium chloride, sodium lactate, sodium pyrrolidonecarboxylate, and zinc pyrrolidonecarboxylate; extracted liquids of plants such as rose, lemon, and lavender; and the like.

Examples of the surfactant include anionic surfactants such as N-long chain acyl amino acid salts including N-long chain acyl acidic amino acid salts such as N-long chain acyl glutamic acid salts and N-long chain acyl aspartic acid salts and N-long chain acyl neutral amino acid salts such as N-long chain acylglycine salts, N-long chain acylalanine salts and N-long chain acylthreonine salts, N-long chain fatty acid acyl-N-methyl taurine salts, alkyl sulfates and alkylene oxide adducts thereof, fatty acid amide ether sulfates, metal salts and weakly basic salts of fatty acids, sulfosuccinate surfactants and alkyl phosphates; amphoteric surfactants such as betaine surfactants including alkylbetaines, alkylamidobetaines, aminopropionates, carboxybetaines and the like, aminocarboxylate surfactants and imidazoline surfactants; cationic surfactants such as aliphatic amine salts including alkyl ammonium chlorides, dialkyl ammonium chlorides and the like, quaternary ammonium salts thereof, aromatic quaternary ammonium salts including benzalkonium salts and the like, fatty acid acyl arginine esters and alkyloxyhydroxypropyl arginine salts; nonionic surfactants such as glycerin fatty acid esters and alkylene glycol adducts thereof, polyglycerine fatty acid esters and alkylene glycol adducts thereof, propylene glycol fatty acid esters and alkylene glycol adducts thereof, butylene glycol fatty acid esters and alkylene glycol adducts thereof, sorbitol fatty acid esters and alkylene glycol adducts thereof, polyalkylene glycol fatty acid esters, sucrose fatty acid esters, glycerine alkyl ethers, polyoxyalkylene alkyl ethers, polyoxyethylene alkyl phenyl ethers, polyoxyethylene hydrogenated castor oils and alkylene glycol adducts of lanoline; and the like.

The ultraviolet light absorber is, for example, an organic substance (a light protection filter), which is in a liquid or crystalline state at room temperature, and capable of absorbing ultraviolet light and releasing the absorbed energy in the form of radiation with a longer wavelength (such as heat). A UV-B filter can be oil-soluble or water-soluble. Examples of the oil-soluble substance include 3-benzylidenecamphor and 3-benzylidenenorcamphor and derivatives thereof, for example, 3-(4-methylbenzylidene)camphor; 4-aminobenzoic acid derivatives, preferably 4-(dimethylamino)benzoic acid 2-ethylhexyl ester, 4-(dimethylamino)benzoic acid 2-octyl ester and 4-(dimethylamino)benzoic acid amyl ester; cinnamic acid esters, preferably 4-methoxycinnamic acid 2-ethylhexyl ester, 4-methoxycinnamic acid propyl ester, 4-methoxycinnamic acid isoamyl ester, 2-cyano-3,3-phenyl-cinnamic acid 2-ethylhexyl ester (octocrylene); salicylic acid esters, preferably salicylic acid 2-ethylhexyl ester, salicylic acid 4-isopropylbenzyl ester, salicylic acid homomethyl ester; benzophenone derivatives, preferably 2-hydroxy-4-methoxybenzophenone, 2-hydroxy-4-methoxy-4'-methyl-benzophenone, 2,2'-dihydroxy-4-methoxybenzophenone; benzalmalonic acid esters, preferably 4-methoxybenzalmalonic acid di-2-ethylhexyl ester; triazine derivatives, for example, 2,4,6-trianilino-(p-carbo-2'-ethyl-1'-hexyloxy)-1,3,5-triazine and octyl triazone, or dioctyl butamido triazone (Uvasorb (registered trademark) HEB); propane-1,3-diones, for example, 1-(4-tert-butylphenyl)-3-(4'-methoxyphenyl) propane-1,3-dione; ketotricyclo(5.2.1.0) decane derivatives; and the like.

Examples of an appropriate water-soluble substance include 2-phenylbenzimidazole-5-sulfonic acid and alkali metal salts thereof, alkaline earth metal salts thereof, ammonium salts thereof, alkylammonium salts thereof, alkanolammonium salts thereof and glucammonium salts thereof; sulfonic acid derivatives of benzophenones, preferably 2-hydroxy-4-methoxybenzophenone-5-sulfonic acid and salts thereof; sulfonic acid derivatives of 3-benzylidenecamphor, for example, 4-(2-oxo-3-bornylidenemethyl)-benzenesulfonic acid and 2-methyl-5-(2-oxo-3-bornylidene)sulfonic acid and salts thereof; and the like. Examples of a common UV-A filter, in particular as benzoylmethane derivatives, include 1-(4'-tert-butylphenyl)-3-(4'-methoxyphenyl)propane-1,3-dione, 4-tert-butyl-4'-methoxydibenzoylmethane (Parsol (registered trademark) 1789), 1-phenyl-3-(4'-isopropylphenyl)-propane-1,3-dione, enamine compounds, and the like.

Examples of the moisturizing agent include mucopolysaccharides, collagen, peptides, keratin and the like.

Other features of the invention will become apparent in the course of the following descriptions of exemplary embodiments which are given for illustration of the invention and are not intended to be limiting thereof.

EXAMPLES

Example 1 to Example 24 and Comparative Examples 1 to 6

Water-in-oil type emulsified compositions (Examples 1 to 24 and Comparative Examples 1 to 6) comprising a compounding formulation described in the following Tables 1 to 5 were prepared. Incidentally, as the (A) N-long chain acyl neutral amino acid ester, N-myristoyl-N-methyl-β-alanine phytosteryl and N-myristoyl-N-methyl-β-alanine decyltetradecyl, and as the (B) silicone oil, dodecamethylcyclohexasiloxane (DC246, Toray Dow Corning Silicone) were used.
Evaluation of Storage Stability of Water-in-Oil Type Emulsified Composition.

The phase state of the compositions was visually observed immediately after preparation of the compositions, after 2 weeks at 40° C., and after 4 weeks at 40° C., and evaluation of stability was carried out based on the following criteria.

○○: Phase separation was not observed after storage at 40° C. for 4 weeks.
○: Phase separation was observed after storage at 40° C. for 4 weeks.
Δ: Phase separation was observed after storage at 40° C. for 2 weeks.
X: Phase separation was observed immediately after preparation at 25° C.

Evaluation of Feeling of Use of Water-in-Oil Type Emulsified Composition.

A sensory evaluation was carried out by 3 special panelists in terms of a feeling of use when any of the prepared water-in-oil type emulsified compositions was applied to the skin, and the water-in-oil type emulsified compositions were evaluated based on the following evaluation criteria. An average value of the evaluation points of 3 special panelists was calculated, and the case where the average value is 0 or higher and lower than 1 was evaluated as X, the case where the average value is 1 or higher and lower than 2 was evaluated as Δ, the case where the average value is 2 or higher and lower than 3 was evaluated as ○, and the case where the average value is 3 or higher and 4 or lower was evaluated as ○○.

4: It is a very smooth and good water-in-oil type emulsified composition.
3: It is a smooth and good water-in-oil type emulsified composition.
2: It is a somewhat smooth water-in-oil type emulsified composition.
1: It is a somewhat hard water-in-oil type emulsified composition with poor spreadability.
0: It is a very hard water-in-oil type emulsified composition with poor spreadability, or is not in the form of a water-in-oil type emulsified composition due to phase separation or the like.

TABLE 1

(Amounts in % by weight)

|  | Example 1 | Example 2 | Example 3 | Example 4 | Example 5 | Example 6 |
|---|---|---|---|---|---|---|
| N-myristoyl-N-methyl-β-alanine phytosteryl | 1.0 | 1.0 | 1.0 | 1.0 | 2.0 | 3.0 |
| N-myristoyl-N-methyl-β-alanine decyltetradecyl | 1.0 | 1.0 | 1.0 | 1.0 | 2.0 | 3.0 |
| Dodecamethyl-cyclohexa-siloxane | 20.0 | 30.0 | 40.0 | 50.0 | 60.0 | 40.0 |
| Water | 78.0 | 68.0 | 58.0 | 48.0 | 36.0 | 54.0 |
| Total | 100.0 | 100.0 | 100.0 | 100.0 | 100.0 | 100.0 |
| Evaluation of storage stability | ○○ | ○○ | ○○ | ○○ | ○○ | ○○ |
| Evaluation of feeling of use | ○○ | ○○ | ○○ | ○○ | ○○ | ○○ |

TABLE 2

(Amounts in % by weight)

| | Example 7 | Example 8 | Example 9 | Example 10 | Example 11 | Example 12 |
|---|---|---|---|---|---|---|
| N-myristoyl-N-methyl-β-alanine phytosteryl | 4.0 | 4.0 | 5.0 | 10.0 | 20.0 | 30.0 |
| N-myristoyl-N-methyl-β-alanine decyltetradecyl | 4.0 | 4.0 | 5.0 | 10.0 | 20.0 | 30.0 |
| Dodecamethyl-cyclohexa-siloxane | 30.0 | 50.0 | 20.0 | 10.0 | 50.0 | 20.0 |
| Water | 62.0 | 42.0 | 70.0 | 70.0 | 10.0 | 20.0 |
| Total | 100.0 | 100.0 | 100.0 | 100.0 | 100.0 | 100.0 |
| Evaluation of storage stability | ○○ | ○○ | ○○ | ○○ | ○○ | ○○ |
| Evaluation of feeling of use | ○○ | ○○ | ○○ | ○○ | ○○ | ○○ |

TABLE 3

(Amounts in % by weight)

| | Example 13 | Example 14 | Example 15 | Example 16 | Example 17 | Example 18 |
|---|---|---|---|---|---|---|
| N-myristoyl-N-methyl-β-alanine phytosteryl | 30.0 | 5.0 | 10.0 | 2.0 | 2.0 | 4.0 |
| N-myristoyl-N-methyl-β-alanine decyltetradecyl | 30.0 | 5.0 | 10.0 | 2.0 | 2.0 | 4.0 |
| Dodecamethyl-cyclohexa-siloxane | 30.0 | 60.0 | 60.0 | 70.0 | 80.0 | 90.0 |
| Water | 10.0 | 30.0 | 20.0 | 26.0 | 16.0 | 2.0 |
| Total | 100.0 | 100.0 | 100.0 | 100.0 | 100.0 | 100.0 |
| Evaluation of storage stability | ○○ | ○○ | ○○ | ○○ | ○○ | ○○ |
| Evaluation of feeling of use | ○○ | ○ | ○ | ○ | ○ | ○ |

TABLE 4

(Amounts in % by weight)

| | Example 19 | Example 20 | Example 21 | Example 22 | Example 23 | Example 24 |
|---|---|---|---|---|---|---|
| N-myristoyl-N-methyl-β-alanine phytosteryl | 10.0 | 40.0 | 0.2 | 0.3 | 0.4 | 0.5 |
| N-myristoyl-N-methyl-β-alanine decyltetradecyl | 10.0 | 40.0 | 0.2 | 0.3 | 0.4 | 0.5 |
| Dodecamethyl-cyclohexa-siloxane | 70.0 | 10.0 | 10.0 | 10.0 | 20.0 | 20.0 |
| Water | 10.0 | 10.0 | 89.6 | 89.4 | 79.2 | 79.0 |
| Total | 100.0 | 100.0 | 100.0 | 100.0 | 100.0 | 100.0 |
| Evaluation of storage stability | ○○ | ○○ | ○ | ○ | ○ | ○ |
| Evaluation of feeling of use | ○ | ○ | ○ | ○ | ○ | ○ |

TABLE 5

(Amounts in % by weight)

|  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|
| Lauroyl glutamate (phytosteryl/octyldodecyl) *1 | 2.0 | 10.0 | — | — | — | — |
| Lauroyl glutamate (phytosteryl/behenyl/octyl-dodecyl) *2 | — | — | 2.0 | 10.0 | — | — |
| Lauroyl glutamate (cholesteryl/behenyl/octyl-dodecyl) *3 | — | — | — | — | 2.0 | 10.0 |
| Dodecamethylcyclohexa-siloxane | 20.0 | 80.0 | 20.0 | 80.0 | 20.0 | 80.0 |
| Water | 79.8 | 9.0 | 19.2 | 29.4 | 39.6 | 49.8 |
| Total | 100.0 | 100.0 | 100.0 | 100.0 | 100.0 | 100.0 |
| Evaluation of storage stability | X | X | X | X | X | X |
| Evaluation of feeling of use | X | X | X | X | X | X |

As is apparent from Tables 1 to 5, water-in-oil type emulsified compositions having a good storage stability and feeling of use could be obtained with the use of (A) an N-long chain acyl neutral amino acid ester, (B) a silicone oil and (C) water (Examples 1 to 24). In contrast, in the case where an N-long chain acyl acidic amino acid ester was used, a water-in-oil type emulsified composition could not be obtained, and separation was caused immediately after preparation in all cases (Comparative Examples 1 to 6).

Examples 25 to 30

Water-in-oil type emulsified compositions (Examples 25 to 30) comprising a compounding formulation described in the following Table 6 were prepared, and the same evaluation was carried out as in Tables 1 to 5. Incidentally, as the (B) silicone oil, decamethylcyclopentasiloxane (SH245, Toray Dow Corning Silicone) was used.

TABLE 6

(Amounts in % by weight)

|  | Example 25 | Example 26 | Example 27 | Example 28 | Example 29 | Example 30 |
|---|---|---|---|---|---|---|
| N-myristoyl-N-methyl-β-alanine phytosteryl | 2.0 | 5.0 | 5.0 | 5.0 | 20.0 | 20.0 |
| N-myristoyl-N-methyl-β-alanine decyltetradecyl | 2.0 | 5.0 | 5.0 | 5.0 | 20.0 | 20.0 |
| Decamethylcyclo-pentasiloxane | 20.0 | 20.0 | 30.0 | 40.0 | 30.0 | 50.0 |
| Water | 76.0 | 70.0 | 60.0 | 50.0 | 30.0 | 10.0 |
| Total | 100.0 | 100.0 | 100.0 | 100.0 | 100.0 | 100.0 |
| Evaluation of storage stability | ○○ | ○○ | ○○ | ○○ | ○○ | ○○ |
| Evaluation of feeling of use | ○○ | ○○ | ○○ | ○○ | ○○ | ○○ |

As is apparent from the results shown in Table 6, water-in-oil type emulsified compositions comprising (A) an N-long chain acyl neutral amino acid ester, (B) a silicone oil and (C) water could be obtained.

Formulation Examples 1 to 3

When sunscreen formulations shown in the following Tables 7 to 9 were prepared according to a conventional method, a good feeling of use and storage stability could be obtained in all cases.

TABLE 7

Formulation Example 1, Sunscreen

|  | (% by weight) |
|---|---|
| N-myristoyl-N-methyl-β-alanine phytosteryl | 1.5 |
| N-myristoyl-N-methyl-β-alanine decyltetradecyl | 1.5 |

TABLE 7-continued

Formulation Example 1, Sunscreen

| | (% by weight) |
|---|---|
| Cyclomethicone | 50.0 |
| Tocopherol acetate | 0.05 |
| Zinc oxide | 8.0 |
| Titanium oxide | 5.0 |
| Butylene glycol | 5.0 |
| Methylparabene | 0.1 |
| PCA-Na | 0.5 |
| Water | Balance |
| | 100.0 |

TABLE 8

Formulation Example 2, Sunscreen

| | (% by weight) |
|---|---|
| N-myristoyl-N-methyl-β-alanine phytosteryl | 1.5 |
| N-myristoyl-N-methyl-β-alanine decyltetradecyl | 1.5 |
| Cyclomethicone | 30.0 |
| Methylpolysiloxane | 2.0 |
| Dimethicone | 2.0 |
| Tocopherol acetate | 0.05 |
| Zinc oxide | 8.0 |
| Titanium oxide | 5.0 |
| Butylene glycol | 5.0 |
| Methylparabene | 0.1 |
| PCA-Na | 0.5 |
| Water | Balance |
| | 100.0 |

TABLE 9

Formulation Example 3, Sunscreen

| | (% by weight) |
|---|---|
| N-myristoyl-N-methyl-β-alanine phytosteryl | 1.5 |
| N-myristoyl-N-methyl-β-alanine decyltetradecyl | 1.5 |
| Cyclomethicone | 10.0 |
| Phenylmethicone | 1.0 |
| Dimethicone | 2.0 |
| Squalane | 2.0 |
| Tocopherol acetate | 0.05 |
| Zinc oxide | 8.0 |
| Titanium oxide | 5.0 |
| Butylene glycol | 5.0 |
| Methylparabene | 0.1 |
| PCA-Na | 0.5 |
| Water | Balance |
| | 100.0 |

INDUSTRIAL APPLICABILITY

It is extremely significant that according to the present invention, by incorporating a specific N-long chain acyl neutral amino acid ester, a silicone oil, and water, a water-in-oil type emulsified cosmetic which is excellent in emulsification stability and whose sticky feeling has been improved can be provided.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A water-in-oil emulsified composition, comprising:
   (A) N-long chain acyl neutral amino acid ester selected from the group consisting of N-myristoyl-N-methyl-β-alanine phytosteryl, N-myristoyl-N-methyl-β-alanine decyltetradecyl, and mixtures thereof
   (B) cyclic silicone oil selected from the group consisting of decamethylcyclopentasiloxane, dodecamethylcyclohexasiloxane, and
   (C) water, wherein water is present in an amount of from 0.1 to 94.6 wt. % based on the total weight of (A), (B), and (C),
   wherein the ratio of (A):(B) ranges from 4:96 to 90:10.

2. The water-in-oil emulsified composition according to claim 1, wherein the weight ratio of (A) to (B) is from 5:95 to 80:20, and (C) is present in an amount of from 0.5 to 90 wt. % based on the total weight of (A), (B), and (C).

3. The water-in-oil emulsified composition according to claim 1, wherein the weight ratio of (A) to (B) is from 5:95 to 80:20.

4. The water-in-oil emulsified composition according to claim 1, wherein the weight ratio of (A) to (B) is from 6:94 to 75:25.

5. The water-in-oil emulsified composition according to claim 2, wherein the weight ratio of (A) to (B) is from 6:94 to 75:25.

6. A cosmetic, comprising a water-in-oil emulsified composition according to claim 1.

7. The cosmetic according to claim 6, further comprising one or more ingredients selected from the group consisting of a hydrocarbon, a higher fatty acid ester, an animal oil, a vegetable oil, a fat, a fluorinated oil, an organic pigment, an inorganic pigment, a water-soluble polymer, an alcohol, a surfactant, an ultraviolet light absorber, a moisturizing agent, an antioxidants, a beautifying component, a preservative, a perfume, and mixtures thereof.

8. The water-in-oil emulsified composition according to claim 1, wherein said cyclic silicone oil is dodecamethylcyclohexasiloxane.

9. The water-in-oil emulsified composition according to claim 1, wherein said cyclic silicone is decamethylcyclopentasiloxane.

10. The water-in-oil emulsified composition according to claim 1, wherein water is present in an amount of from 0.5 to 90 wt. % based on the total weight of (A), (B), and (C).

11. The water-in-oil emulsified composition according to claim 1, wherein water is present in an amount of from 1.0 to 80 wt. % based on the total weight of (A), (B), and (C).

12. The water-in-oil emulsified composition according to claim 2, wherein water is present in an amount of from 1.0 to 80 wt. % based on the total weight of (A), (B), and (C).

* * * * *